United States Patent
Wu et al.

(10) Patent No.: US 9,933,299 B2
(45) Date of Patent: Apr. 3, 2018

(54) WEARABLE ILLUMINATION ACTIVITY RECORDING APPARATUS HAVING A LIGHT SENSING UNIT AND A MOTION SENSING UNIT

(71) Applicants: Ming-Han Wu, Kaohsiung (TW); Si-Yi Wu, Kaohsiung (TW)

(72) Inventors: Ming-Han Wu, Kaohsiung (TW); Si-Yi Wu, Kaohsiung (TW)

( * ) Notice: Subject to any disclaimer, the term of this patent is extended or adjusted under 35 U.S.C. 154(b) by 0 days.

(21) Appl. No.: 15/122,462

(22) PCT Filed: Jul. 1, 2014

(86) PCT No.: PCT/CN2014/081334
§ 371 (c)(1),
(2) Date: Aug. 30, 2016

(87) PCT Pub. No.: WO2016/000199
PCT Pub. Date: Jan. 7, 2016

(65) Prior Publication Data
US 2017/0131141 A1     May 11, 2017

(51) Int. Cl.
*G01J 1/42* (2006.01)
*G01J 1/02* (2006.01)
(Continued)

(52) U.S. Cl.
CPC .......... *G01J 1/4204* (2013.01); *A61B 5/0004* (2013.01); *A61B 5/1118* (2013.01);
(Continued)

(58) Field of Classification Search
CPC ... A61B 5/1118; A61B 5/0004; A61B 5/6803; A61B 5/681; G01J 1/4204; G01P 13/00
(Continued)

(56) References Cited

U.S. PATENT DOCUMENTS 5,834,765 A * 11/1998 Ashdown .................. G01J 1/04
250/214 AL
2006/0289779 A1   12/2006 Marmaropoulos
2012/0212938 A1   8/2012 Nguyen et al.

FOREIGN PATENT DOCUMENTS

CN        2101222 U      4/1992
CN        2586998 Y      11/2003
(Continued)

*Primary Examiner* — Que T Le
(74) *Attorney, Agent, or Firm* — Alan D. Kamrath; Kamrath IP Lawfirm, P.A.

(57) ABSTRACT

A wearable illumination activity recording apparatus (1) includes a processing unit (11), a light sensing unit (12) and a motion sensing unit (13). The light sensing unit (12) is electrically connected to the processing unit (11) and outputs a light sensing signal (LS) to the processing unit (11). The motion sensing unit (13) is electrically connected to the processing unit (11) and outputs a motion sensing signal (MS) to the processing unit (11). The processing unit (11) determines whether the wearable illumination activity recording apparatus (1) is indoors or outdoors according to the light sensing signal (LS), and determines whether the wearable illumination activity recording apparatus (1) is in motion or not according to the motion sensing signal (MS). When the wearable illumination activity recording apparatus (1) is outdoors and in motion, the processing unit (11) records an illumination-receiving time.

11 Claims, 2 Drawing Sheets

(51) Int. Cl.
*A61B 5/11* (2006.01)
*A61B 5/00* (2006.01)
*G01P 13/00* (2006.01)

(52) U.S. Cl.
CPC ............ *A61B 5/1122* (2013.01); *A61B 5/486* (2013.01); *A61B 5/681* (2013.01); *A61B 5/6803* (2013.01); *A61B 5/6807* (2013.01); *A61B 5/746* (2013.01); *G01J 1/0219* (2013.01); *G01P 13/00* (2013.01); *A61B 2560/0242* (2013.01); *A61B 2562/0219* (2013.01)

(58) Field of Classification Search
USPC .............................. 250/214 AL, 214 R, 221
See application file for complete search history.

(56) References Cited

FOREIGN PATENT DOCUMENTS

| | | |
|---|---|---|
| CN | 203259714 U | 10/2013 |
| CN | 103868589 A | 6/2014 |

\* cited by examiner

WEARABLE ILLUMINATION ACTIVITY RECORDING APPARATUS HAVING A LIGHT SENSING UNIT AND A MOTION SENSING UNIT

BACKGROUND OF THE INVENTION

Field of the Invention

The invention relates to a recording apparatus and, in particular, to a wearable illumination activity recording apparatus.

Description of the Prior Art

Since moderns live a fast-paced life and students get more and more stresses from heavy schoolwork recently, people normally can't accept sufficient illumination. According to research, receiving sufficient illumination will bring many benefits, such as producing vitamin D, making people feel good in mood, promoting blood circulation, enhancing metabolism and preventing nearsightedness/myopia.

Therefore, it is an important subject to provide an illumination activity recording apparatus to help users receive sufficient illumination so as to further enhance the health of people.

SUMMARY OF THE INVENTION

In view of the foregoing subject, an objective of the invention is to provide a wearable illumination activity recording apparatus to help users receive sufficient illumination so as to further enhance the health of people and besides to be wearable for users.

To achieve the above objective, a wearable illumination activity recording apparatus of the invention includes a processing unit, a light sensing unit and a motion sensing unit.

The light sensing unit is electrically connected to the processing unit and outputs a light sensing signal to the processing unit. The motion sensing unit is electrically connected to the processing unit and outputs a motion sensing signal to the processing unit. The processing unit determines whether the wearable illumination activity recording apparatus is indoors or outdoors according to the light sensing signal, and determines whether the wearable illumination activity recording apparatus is in motion or not according to the motion sensing signal. When the wearable illumination activity recording apparatus is outdoors and in motion, the processing unit records an illumination-receiving time.

In one embodiment, the wearable illumination activity recording apparatus is a watch, a bracelet device, a head-mounted apparatus, a necklace device, an armband device, a waist-worn device or a shoe-worn device or the like wearable in the body.

In one embodiment, the light sensing unit includes a photoresistor, a photodiode, a phototransistor, a solar cell device or any of their combinations.

In one embodiment, the motion sensing signal contains the information of acceleration, velocity, angular velocity, angle, or displacement or their any combination.

In one embodiment, the motion sensing unit includes an accelerometer, a gyroscope or their combination.

In one embodiment, the processing unit generates a luminous flux information or an illuminance information according to the light sensing signal to determine whether the wearable illumination activity recording apparatus is indoors or outdoors.

In one embodiment, the processing unit generates an acceleration information, a velocity information, an angular velocity information, a displacement information or an angle information according to the motion sensing signal to determine whether the wearable illumination activity recording apparatus is in motion or not.

In one embodiment, the processing unit further records a luminous flux or an illuminance which is corresponding to the illumination-receiving time.

In one embodiment, the processing unit further adjusts an illumination-receivable time according to the luminous flux or illuminance.

In one embodiment, the wearable illumination activity recording apparatus further comprises a warning unit electrically connected with the processing unit. The processing unit compares an illumination-ending time with a current time to output an enabling signal to the warning or reminding unit so that the warning or reminding unit emits a warning or reminding.

In one embodiment, the wearable illumination activity recording apparatus further comprises a wireless communication unit electrically connected to the processing unit to transmit the illumination-receiving time.

As mentioned above, the wearable illumination activity recording apparatus of the invention includes a light sensing unit to sense the light and a motion sensing unit to sense the motion. The processing unit determines whether the wearable illumination activity recording apparatus is indoors or outdoors according to the light sensing signal outputted by the light sensing unit, and determines whether the wearable illumination activity recording apparatus is in motion or not according to the motion sensing signal outputted by the motion sensing unit. When the wearable illumination activity recording apparatus is outdoors and in motion, it represents the user is receiving illumination, and thus the processing unit records an illumination-receiving time. The processing unit also can provide many applications according to the illumination-receiving time, applications such as warning or reminding the user if the illumination-receiving amount is insufficient or excessive, or warning the user if the illumination intensity is overhigh. Therefore, the wearable illumination activity recording apparatus of the invention can help users receive sufficient illumination so as to further enhance the health of people and besides to be wearable for users.

DETAILED DESCRIPTION OF THE INVENTION

Figure 1:
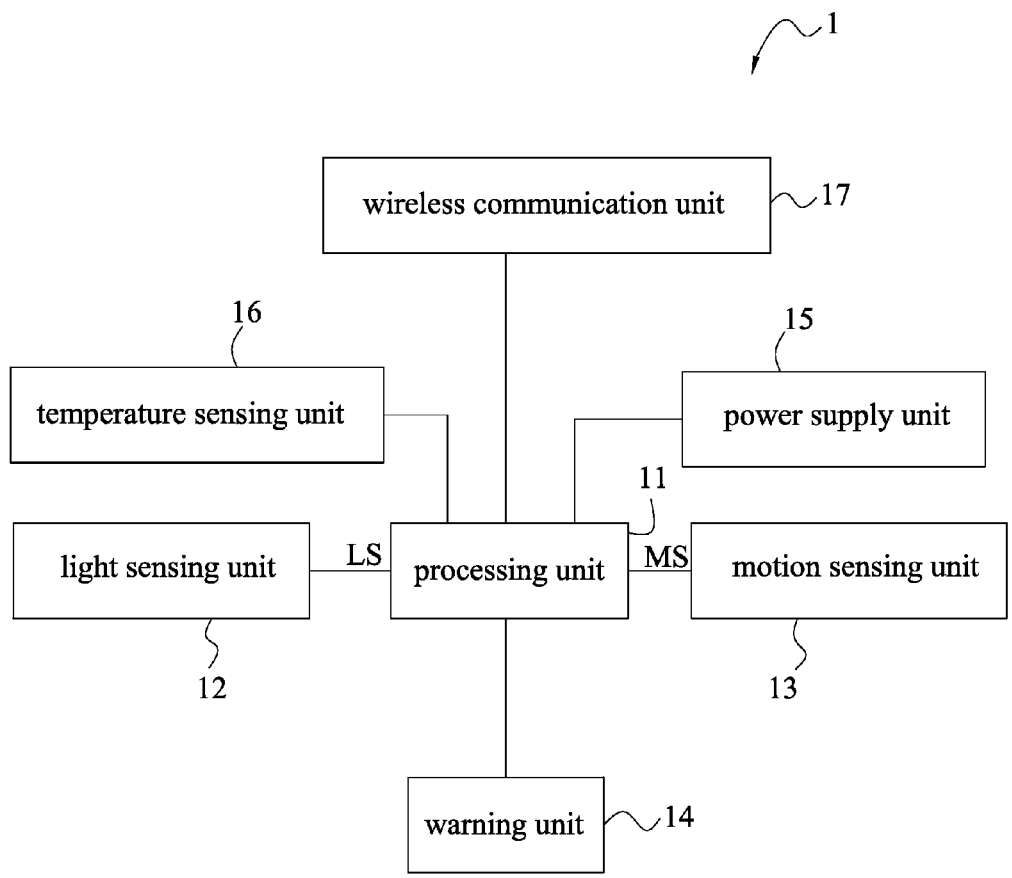
FIG. 1 is a schematic block diagram of a wearable illumination activity recording apparatus according to an embodiment of the invention.

FIG. 1 is a schematic block diagram of a wearable illumination activity recording apparatus 1 according to an embodiment of the invention. As shown in FIG. 1, the wearable illumination activity recording apparatus 1 includes a processing unit 11, a light sensing unit 12 and a motion sensing unit 13. The wearable illumination activity recording apparatus 1 can be worn by the user and can be embodied as a watch, a bracelet device, a head-mounted apparatus, a necklace device, an armband device, a waist-worn device or a shoe-worn device, but this invention is not limited thereto. The wearable illumination activity recording apparatus 1 can record the time that the user receives illumination and thus provide smart applications, such as computing the illumination-receiving amount, warning or reminding the user of insufficient or excessive illumination-receiving amount, warning the user of overhigh illumination intensity, but this invention is not limited thereto.

The light sensing unit 12 is electrically connected to the processing unit 11 and outputs a light sensing signal LS to the processing unit 11. The light sensing unit 12 senses the outside light and includes, for example, a photoresistor, a photodiode, a phototransistor, a solar cell device or other kinds of optoelectronic devices, or their any combination.

The said devices can convert the sensed light into electric signals. Moreover, the light sensing unit 12 can further include a filter element (not shown), which can filter out the undesired light so as to enhance the light sensing efficiency. For example, the filter element can filter out the infrared or visible light, so that the ultraviolet light can become the majority of the sensed light to benefit the determination about the outdoor or indoor case.

The motion sensing unit 13 is electrically connected to the processing unit 11 and outputs a motion sensing signal MS to the processing unit 11. The motion sensing unit 13 can sense the motion of the wearable illumination activity recording apparatus 1 and include an accelerometer, a gyroscope or their combination for example. The motion sensing signal contains the information of acceleration, velocity, angular velocity, angle, or displacement or their any combination for example. Besides, the motion sensing unit 13 may include a computing element to convert one of the above-mentioned information into another kind of information.

The processing unit 11 can process the signals outputted by the light sensing unit 12 and the motion sensing unit 13, and includes a central processing unit (CPU), a microprocessor control unit (MCU) or other processing devices, or their any combination. The processing unit 11 determines whether the wearable illumination activity recording apparatus 1 is indoors or outdoors according to the light sensing signal LS. Many mechanisms can be used to determine whether the wearable illumination activity recording apparatus 1 is indoors or outdoors. For example, the processing unit 11 generates a luminous flux information, an illuminance information or other kinds of light intensity information according to the light sensing signal LS to determine whether the wearable illumination activity recording apparatus 1 is indoors or outdoors. The luminous flux information or the illuminance information represents the illumination intensity, and the illumination intensity also can be represented by other parameters. The processing unit 11 can compare the luminous flux information or the illuminance information with a predetermined value to determine whether the wearable illumination activity recording apparatus 1 is indoors or outdoors. For example, if the luminous flux information or the illuminance information is greater than the predetermined value at the noon, it is determined that the wearable illumination activity recording apparatus 1 is located outdoors. To be noted, the said predetermined value can be changed with time.

The processing unit 11 determines whether the wearable illumination activity recording apparatus 1 is in motion or not according to the motion sensing signal MS. Many mechanisms can be used to determine whether the wearable illumination activity recording apparatus 1 is in motion or not. For example, the processing unit 11 generates an acceleration information, a velocity information, an angular velocity information, a displacement information or an angle information according to the motion sensing signal MS to determine whether the wearable illumination activity recording apparatus 1 is in motion or not. The processing unit 11 can compare at least one of the above information with a predetermined value. If the information is greater than the predetermined value, it is determined that the wearable illumination activity recording apparatus 1 is in motion. The predetermined value can be set according to the age or sex of the user.

When the wearable illumination activity recording apparatus 1 is outdoors and in motion, the processing unit 11 records an illumination-receiving time, which can be accumulated. By the record of the illumination-receiving time, the wearable illumination activity recording apparatus 1 can provide many applications, as illustrated as below.

The processing unit 11 can warn the user according to the illumination-receiving time, and, for example, warn the user when the illumination-receiving time is insufficient or excessive. In one embodiment, the wearable illumination activity recording apparatus 1 can further include a warning unit 14, which is electrically connected with the processing unit 11 and can send a warning, such as text, sound, image, video, flash, vibration or their any combination. The warning unit 14 includes a speaker, a display, a flasher, a vibrator or their any combination.

In one embodiment, the processing unit 11 can further record a luminous flux or an illuminance which is corresponding to the illumination-receiving time. Herein, the luminous flux is equal to photo energy/time (J/s), and the illuminance is equal to luminous flux/area. By the offering of the luminous flux or illuminance, the wearable illumination activity recording apparatus 1 can provide a comparison chart between the illumination-receiving time and the luminous flux or illuminance. Moreover, the wearable illumination activity recording apparatus 1 can further provide an illumination-receiving amount, which is equal to the illumination-receiving time multiplying the luminous flux or illuminance. When the luminous flux or illuminance is greater than a predetermined value, it can indicate the illumination intensity is too high and thus harmful to health. Therefore, the warning unit 14 can emit a warning to warn the user. The said predetermined value can be changed with time. When the illumination-receiving amount is enough, excessive or up to a certain level, the warning unit 14 can emit a warning to warn the user. Moreover, the processing unit 11 can further adjust an illumination-receivable time (that the user should spend to receive illumination) according to the luminous flux or illuminance. For example, when the illumination intensity of a certain day is greater than normal, the illumination-receivable time of the day can be cut down. The illumination-receivable time can be set up by the user originally and then adjusted by the processing unit 11. If the illumination-receivable time is about to be reached, the warning unit 14 can send a warning to warn the user.

The processing unit 11 can compare an illumination-ending time with a current time to output an enabling signal to the warning unit 14 so that the warning unit 14 can emit a warning. Herein, the illumination-ending time denotes the time of sunset. The warning unit 14 can emit a warning when the illumination-ending time is about to be reached, to warn the user to grasp the opportunity for receiving illumination.

In this embodiment, the wearable illumination activity recording apparatus 1 can further include a power supply unit 15, which can supply power to all the elements of the wearable illumination activity recording apparatus 1. The warning unit 14 also can send a warning when the less power occurs or the idle time is too long.

In this embodiment, the wearable illumination activity recording apparatus 1 can further include a temperature sensing unit 16, which is electrically connected to the processing unit 11. The temperature sensing unit 16 can assist in the determination of the outdoor or indoor case or in other purposes, such as temperature indication.

In this embodiment, the wearable illumination activity recording apparatus 1 can further include a wireless communication unit 17, which is electrically connected to the processing unit 11 and can at least transmit the illumination-receiving time. Moreover, the wireless communication unit 17 can further transmit any of the above-mentioned information for the analysis implemented by the doctor or professional.

Figure 2:
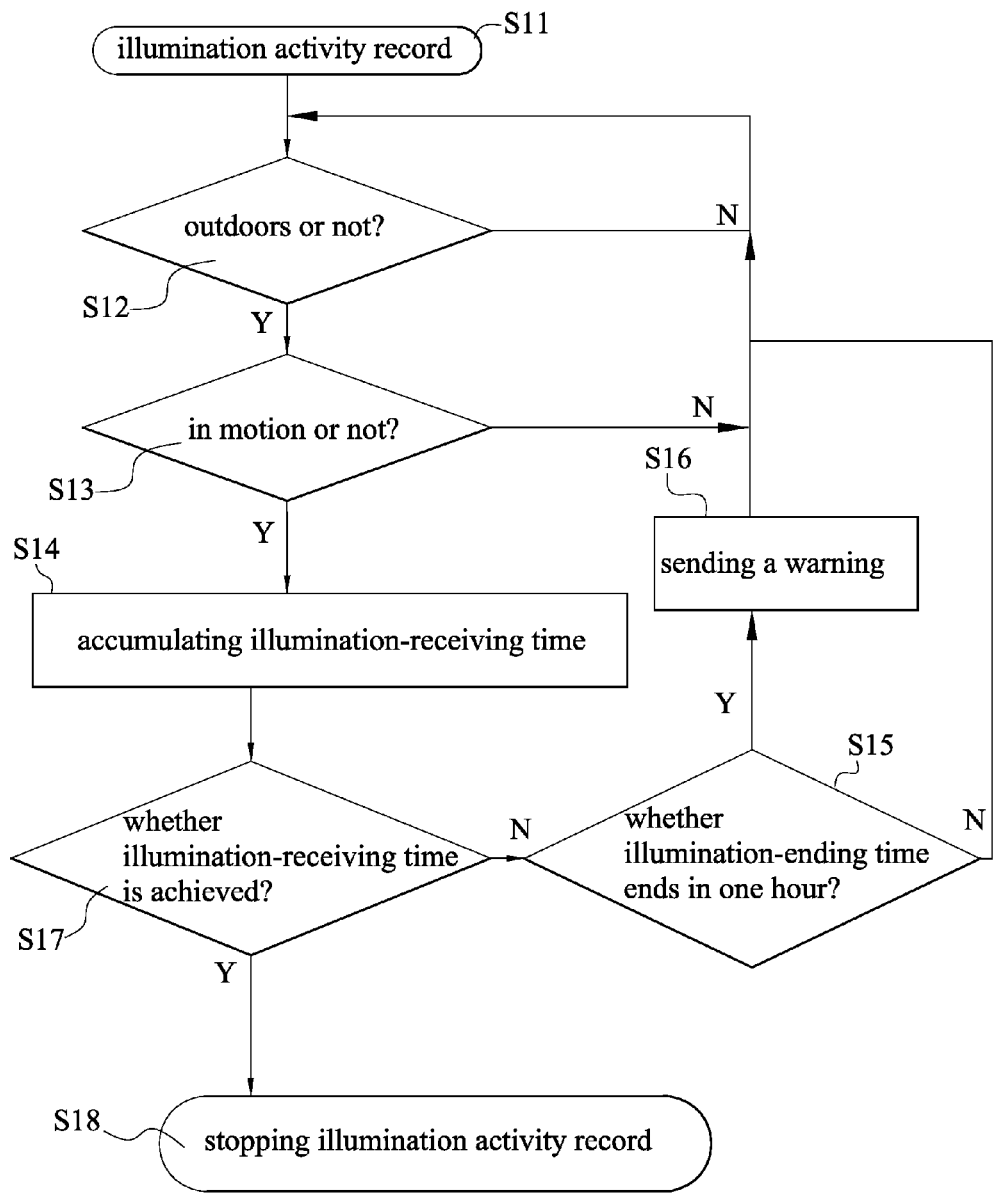
FIG. 2 is a schematic flowchart of the wearable illumination activity recording apparatus according to an embodiment of the invention.

FIG. 2 is a schematic flowchart of the wearable illumination activity recording apparatus 1 according to an embodiment of the invention. As shown in FIG. 2, first, an illumination activity record is opened (S11). Then, it is determined whether the wearable illumination activity recording apparatus 1 is outdoors or not (S12). If the wearable illumination activity recording apparatus 1 is determined as located outdoors, it is determined whether the wearable illumination activity recording apparatus 1 is in motion or not (S13). Then, it is determined whether the illumination-receiving time is achieved or not (S17). If the result of the step S17 is yes, the illumination activity record is stopped (S18). If the result is no, a warning is sent (S16) when the daytime (illumination-ending time) ends in one hour. Certainly, the said "one hour" is just for the illustration but not for limiting the scope of the invention, and it can be changed according to the actual requirements. Moreover, when the daytime (illumination-ending time) ends, a warning also can be sent to warn the user. If the result of the step S15 is no, the process will go back to the step S12 to determine whether the wearable illumination activity recording apparatus 1 is indoors or outdoors.

Summarily, the wearable illumination activity recording apparatus of the invention includes a light sensing unit to sense the light and a motion sensing unit to sense the motion. The processing unit determines whether the wearable illumination activity recording apparatus is indoors or outdoors according to the light sensing signal outputted by the light sensing unit, and determines whether the wearable illumination activity recording apparatus is in motion or not according to the motion sensing signal outputted by the motion sensing unit. When the wearable illumination activity recording apparatus is outdoors and in motion, it represents the user is receiving illumination, and thus the processing unit records an illumination-receiving time. The processing unit also can provide many applications according to the illumination-receiving time, applications such as warning the user if the illumination-receiving amount is insufficient or excessive, or warning the user if the illumination intensity is overhigh. Therefore, the wearable illumination activity recording apparatus of the invention can help users receive sufficient illumination so as to further enhance the health of citizens and national power and besides to be wearable for users.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

The invention claimed is:

1. A wearable illumination activity recording apparatus, comprising:
    a processing unit;
    a light sensing unit electrically connected to the processing unit and outputting a light sensing signal to the processing unit; and
    a motion sensing unit electrically connected to the processing unit and outputting a motion sensing signal to the processing unit,
    wherein the processing unit determines whether the wearable illumination activity recording apparatus is indoors or outdoors according to the light sensing signal, and determines whether the wearable illumination activity recording apparatus is in motion or not according to the motion sensing signal, and when the wearable illumination activity recording apparatus is outdoors and in motion, the processing unit records an illumination-receiving time.

2. The wearable illumination activity recording apparatus as recited in claim 1, which is a watch, a bracelet device, a head-mounted apparatus, a necklace device, an armband device, a waist-worn device or a shoe-worn device.

3. The wearable illumination activity recording apparatus as recited in claim 1, wherein the light sensing unit includes a photoresistor, a photodiode, a phototransistor, a solar cell device or any of their combinations.

4. The wearable illumination activity recording apparatus as recited in claim 1, wherein the motion sensing signal contains the information of acceleration, velocity, angular velocity, angle, or displacement or their any combination.

5. The wearable illumination activity recording apparatus as recited in claim 1, wherein the motion sensing unit includes an accelerometer, a gyroscope or their combination.

6. The wearable illumination activity recording apparatus as recited in claim 1, wherein the processing unit generates a luminous flux information or an illuminance information according to the light sensing signal to determine whether the wearable illumination activity recording apparatus is indoors or outdoors.

7. The wearable illumination activity recording apparatus as recited in claim 1, wherein the processing unit generates an acceleration information, a velocity information, an angular velocity information, a displacement information or an angle information according to the motion sensing signal to determine whether the wearable illumination activity recording apparatus is in motion or not.

8. The wearable illumination activity recording apparatus as recited in claim 1, wherein the processing unit further records a luminous flux or an illuminance which is corresponding to the illumination-receiving time.

9. The wearable illumination activity recording apparatus as recited in claim 8, wherein the processing unit further adjusts an illumination-receivable time according to the luminous flux or illuminance.

10. The wearable illumination activity recording apparatus as recited in claim 1, further comprising:
    a warning unit electrically connected with the processing unit, wherein the processing unit compares an illumination-ending time with a current time to output an enabling signal to the warning unit so that the warning unit emits a warning.

11. The wearable illumination activity recording apparatus as recited in claim 1, further comprising:

a wireless communication unit electrically connected to the processing unit to transmit the illumination-receiving time.

\* \* \* \* \*